(12) United States Patent
Noh et al.

(10) Patent No.: US 9,841,365 B2
(45) Date of Patent: Dec. 12, 2017

(54) STRAIN INSPECTION DEVICE AND ATTACHING METHOD THEREOF

(71) Applicant: LG ELECTRONICS INC., Seoul (KR)

(72) Inventors: Hanna Noh, Seoul (KR); Injoong Kim, Seoul (KR); Sungsuu Kim, Seoul (KR); Gayoung Ryu, Seoul (KR); Youngho Cha, Seoul (KR); Joungwook Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/146,493

(22) Filed: May 4, 2016

(65) Prior Publication Data
US 2016/0370270 A1  Dec. 22, 2016

(30) Foreign Application Priority Data

Jun. 17, 2015  (KR) .................. 10-2015-0086057

(51) Int. Cl.
    *G01N 3/34*  (2006.01)
    *G01N 3/20*  (2006.01)
    *G01N 33/00* (2006.01)

(52) U.S. Cl.
    CPC .............. *G01N 3/34* (2013.01); *G01N 3/20* (2013.01); *G01N 2033/0078* (2013.01); *G01N 2203/0066* (2013.01); *G01N 2203/06* (2013.01)

(58) Field of Classification Search
    CPC .. G01N 3/34; G01N 3/00; G01N 3/02; G01N 1/18; H05K 1/00

USPC ............................................. 73/799
    See application file for complete search history.

(56) References Cited

U.S. PATENT DOCUMENTS

| 6,520,024 B2 * | 2/2003 | Nihei ................ G01B 5/30 |
| | | 73/799 |
| 7,377,177 B1 * | 5/2008 | Lamb ................ G01L 19/147 |
| | | 73/756 |
| 8,157,945 B2 * | 4/2012 | Higuchi .............. B32B 7/06 |
| | | 156/247 |

(Continued)

FOREIGN PATENT DOCUMENTS

| JP | 09-005175 | 1/1997 |
| JP | 2009-014561 | 1/2009 |
| JP | 4260615 | 4/2009 |

(Continued)

OTHER PUBLICATIONS

International Search Report dated Sep. 1, 2016 issued in Application No. PCT/KR2016/004678 (Full English Text).

(Continued)

*Primary Examiner* — Lisa Caputo
*Assistant Examiner* — Octavia Hollington
(74) *Attorney, Agent, or Firm* — KED & Associates, LLP (57) ABSTRACT

A strain inspection device of a printed circuit board (PCB) which is easily cracked or damaged by external pressure (force) applied to the PCB while the PCB is being assembled, and an attaching method thereof. The strain inspection device of a printed circuit board (PCB) includes a fixing member; and a damage indicator fixed to the PCB by the fixing member, having a crack guide through hole, and cracked or damaged along a corner of the crack guide through hole due to deformation of the PCB.

17 Claims, 7 Drawing Sheets

(56) References Cited

U.S. PATENT DOCUMENTS 8,563,869 B2 * 10/2013 Kaga .................. H01L 23/15
174/252

FOREIGN PATENT DOCUMENTS

| JP | 5192095 | 5/2013 |
|----|---------|--------|
| KR | 10-0888855 | 3/2009 |
| KR | 10-1383041 | 4/2014 |

OTHER PUBLICATIONS

Korean Office Action dated Jun. 21, 2016 issued in Application No. 10-2015-0086057.
Korean Notice of Allowance dated Dec. 1, 2016 issued in Application No. 10-2015-0086057.

* cited by examiner

| Force (N) | Strain (µε) | First time | Second time | Third time |
|---|---|---|---|---|
| 36 | 1100 | O | O | O |
| 30 | 1000 | X | X | X |

O: Crack
X: No Crack

FIG. 5

| Feature | Size | | Breaking strain |
|---|---|---|---|
| | L / W / T / D (mm) 7.0 / 3.0 / 0.08 / 1.4 | | Strain (µε) |
| Diamond Hole | ◇ | | 970 |
| Diamond Dog Bone | ⋈ | | 1100 |
| Circle Hole | ○ | | 1540 |
| Circle Dog Bone | )( | | 2260 |

FIG. 6

|  | A | B | C | D | E |
|---|---|---|---|---|---|
| L (mm) | 7.0 | 7.0 | 7.0 | 7.0 | 7.0 |
| W (mm) | 3.0 | 3.0 | 3.0 | 3.0 | 3.0 |
| T (mm) | 0.08 | 0.08 | 0.08 | 0.1 | 0.08 |
| Dx (mm) | 2.0 | 1.8 | 0.3 | 0.4 | 0.1 |
| Dy (mm) | 2.0 | 1.8 | 0.6 | 0.8 | 0.2 |
| SENSOR VALUE | 300 | 350 | 400 | 550 | 1200 |

STRAIN INSPECTION DEVICE AND ATTACHING METHOD THEREOF

CROSS-REFERENCE TO RELATED APPLICATION

Pursuant to 35 U.S.C. §119(a), this application claims the benefit of earlier filing date and right of priority to Korean Application No. 10-2015-0086057, filed on Jun. 17, 2015, the contents of which is incorporated by reference herein in its entirety.

BACKGROUND OF THE INVENTION

1. Field of the Invention

The present disclosure relates to a strain inspection device of a printed circuit board (PCB) and an attaching method thereof.

2. Background of the Invention

In general, a strain gauge is used to measure mechanical damage to a PCB caused by pressure (force) repeatedly applied to the PCB when a component mounted on the PCB is assembled.

SUMMARY OF THE INVENTION

To achieve these and other advantages and in accordance with the purpose of this specification, as embodied and broadly described herein, a strain inspection device of a printed circuit board (PCB) includes: a first fixing member; and a damage indicator fixed to the PCB by the first fixing member, having a crack guide through hole, and cracked or damaged along a corner of the crack guide through hole due to deformation of the PCB.

In an example related to the present disclosure, one or more corners of the crack guide through hole may be positioned to face the sides of the damage indicator.

In an example related to the present disclosure, the crack guide through hole may be a square through hole formed in one region of the damage indicator.

In an example related to the present disclosure, the crack guide through hole may be a diamond-shaped through hole formed in one region of the damage indicator.

In an example related to the present disclosure, an angle between a line linking corners of the crack guide through hole opposing each other and the sides of the damage indicator may be a right angle.

In an example related to the present disclosure, the crack guide through hole may be formed at the center of the damage indicator.

In an example related to the present disclosure, a direction of a first pair of corners of the crack guide through hole opposing each other may be positioned as a length direction of the damage indicator, and a direction of a second pair of corners of the crack guide through hole may be positioned as a width direction of the damage indicator.

In an example related to the present disclosure, the crack guide through hole may be a through hole having a plurality of corners.

In an example related to the present disclosure, the crack guide through hole may be formed in plurality at uniform intervals on the damage indicator.

In an example related to the present disclosure, one or a plurality of crack guide through holes may be formed at uniform intervals on the damage indicator in a length direction of the damage indicator.

In an example related to the present disclosure, one or a plurality of crack guide through holes may be formed at different intervals on the damage indicator in a length direction of the damage indicator.

In an example related to the present disclosure, the device may further include: a second fixing member attached to the first fixing member such that the second fixing member covers both edges of the damage indicator in a length direction.

In an example related to the present disclosure, the first fixing member may be an adhesive or a bonding agent fixing the damage indictor to the PCB.

In an example related to the present disclosure, the first fixing member may be a film type thermosetting bonding agent or an epoxy resin bonding agent.

In an example related to the present disclosure, a material of the damage indicator may be any one of glass, silicon wafer, plaster, and plastic.

To achieve these and other advantages and in accordance with the purpose of this specification, as embodied and broadly described herein, a method for attaching a strain inspection device of a printed circuit board (PCB) includes: forming a crack guide through hole having a corner on a glass plate; and fixedly attaching the glass plate with the crack guide through hole formed thereon to the PCB by using a bonding agent or an adhesive such that the glass plate is cracked along the corner of the crack guide through hole due to deformation of the PCB.

Further scope of applicability of the present application will become more apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

The terminology used herein is for the purpose of describing particular embodiments only and is not intended to be limiting of the invention. Unless otherwise defined, all terms used herein have the same meaning as commonly understood by one of ordinary skill in the art to which this invention pertains, and should not be interpreted as having an excessively comprehensive meaning nor as having an excessively contracted meaning. If technical terms used herein is erroneous that fails to accurately express the technical idea of the present invention, it should be replaced with technical terms that allow the person in the art to properly understand. The general terms used herein should be interpreted according to the definitions in the dictionary or in the context and should not be interpreted as an excessively contracted meaning.

As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, steps, operations, elements, components, and/or groups thereof.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention.

The exemplary embodiments of the present invention will now be described with reference to the accompanying drawings, in which like numbers refer to like elements throughout.

Also, in describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings.

Hereinafter, a strain inspection device of a printed circuit board (PCB), which is capable of easily and promptly checking strain (for example, mechanical damage) that occurs due to pressure (force) applied to a PCB during assembling of the PCB, during a process of manufacturing the PCB, and which is easily cracked or damaged by pressure (force) applied to the PCB, and a method for manufacturing the same will be described.

Figure 1A:
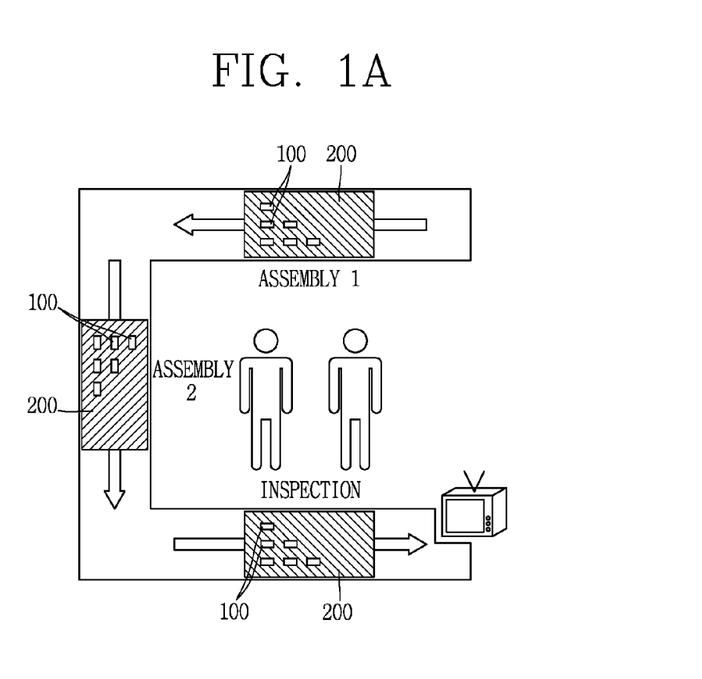
FIG. 1A is a view illustrating a process of assembling and inspecting a printed circuit board (PCB) according to embodiments of the present disclosure.

FIG. 1A is a view illustrating a process of assembling and inspecting a printed circuit board (PCB) according to embodiments of the present disclosure.

As illustrated in FIG. 1A, a PCB 200 is assembled through several stages and undergoes an inspection process. Here, circuit patterns of the PCB 200 and electric and electronic components of the PCB 200 may be damaged by pressure (force) applied to the PCB 200. For example, during a component assembling process including several stages, a component mounting device picks up several electric element components and mounts the picked electric element components on the PCB 200 or inserts the picked electric element components into through holes formed in the PCB 200. Here, the component mounting device applies appropriate force to allow the several electric element components to be placed at accurate positions, and thus, the PCB 200 is repeatedly pressed to be bent. Thus, the circuit patterns of the PCB 200 and the electric and electronic components of the PCB 200 may be damaged according to a degree of bending or strain of the PCB 200 caused by eternal pressure (force) applied during the assembling process including several stages.

In general, in the component mounting process of the PCB, strain causing the PCB to be deformed and damaged during the component mounting process of the PCB is managed on the basis of about 1000µε, and it is required to easily determine whether the PCB is damaged with naked eyes.

Thus, a degree of damage to the PCB 200 may be easily and quickly estimated by using a strain inspection device of a PCB (hereinafter, referred to simply as a "PCB strain inspection device 100".

Figure 1B:
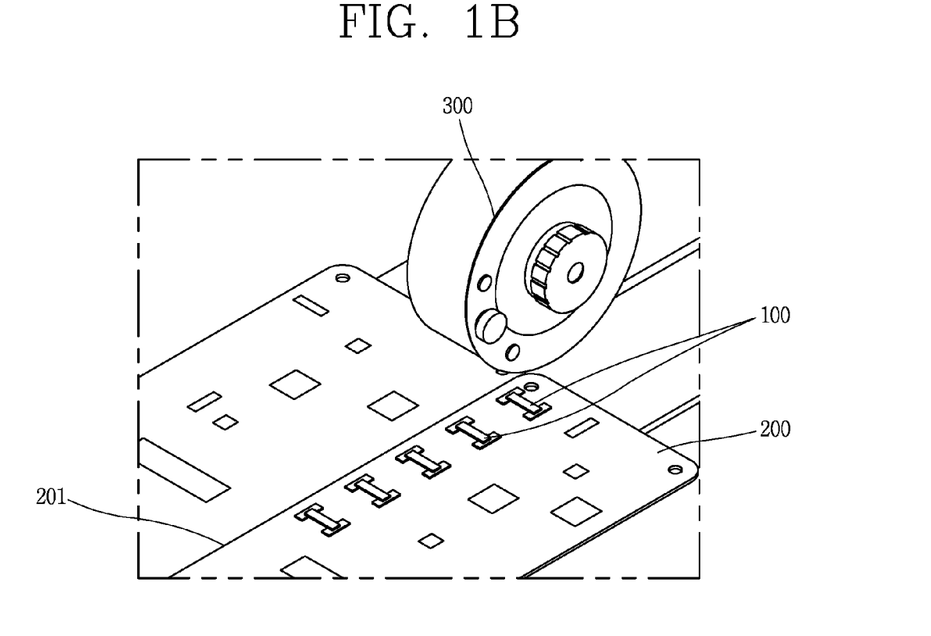
FIG. 1B is a view illustrating a disposition position of a strain inspection device of a PCB according to embodiments of the present disclosure.

FIG. 1B is a view illustrating a disposition position of the PCB strain inspection device 100 according to embodiments of the present disclosure.

As illustrated in FIG. 1B, a plurality of PCB strain inspection devices 100 may be disposed in positions of an area of the entire surface of the PCB 200 to which the largest amount of external pressure (force) is applied when the PCB 200 is assembled. For example, when it is assumed that a plurality of PCBs 200 formed for mass-production are cut along a cutting line 201 by using a cutting tool 300 and the cutting position (cutting line) 201 is a position at which the PCBs 200 are bent maximally, the plurality of PCB strain inspection devices 100 may be disposed along the cutting position (cutting line) 201.

Figure 2A:
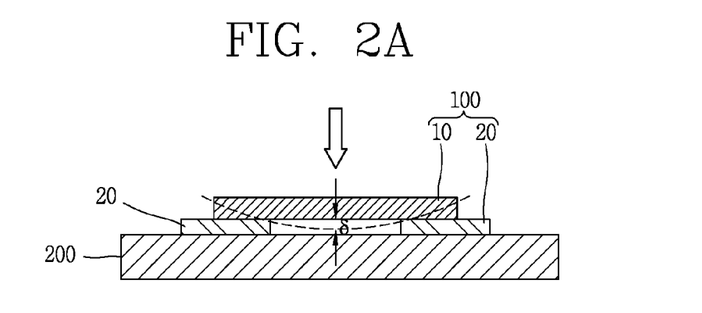
FIG. 2A is a side view illustrating a strain inspection device of a PCB according to an embodiment of the present disclosure.

FIG. 2A is a side view illustrating a strain inspection device of a PCB according to an embodiment of the present disclosure.

Figure 2B:
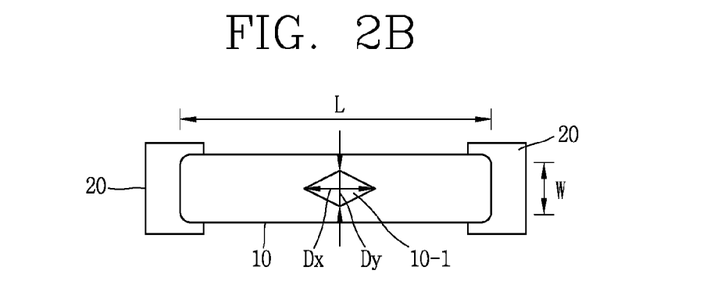
FIG. 2B is a top view illustrating a strain inspection device of a PCB according to an embodiment of the present disclosure.

FIG. 2B is a top view illustrating a strain inspection device of a PCB according to an embodiment of the present disclosure.

As illustrated in FIGS. 2A and 2B, the PCB strain inspection device 100 according to an embodiment of the present invention includes a fixing member 20 and a damage indicator 10 fixed to the PCB 200 by the fixing member 20, having a crack guide through hole 10-1, and cracked (or damaged) along the corners (or sharp edges) of the crack guide through hole 10-1 due to bending (or deflection) of the PCB 200. A PCB inspector may easily and quickly estimate a degree of damage of the PCB 200 upon checking a degree of crack or damage of the damage indicator 10.

A material of the damage indictor 10 may be glass, silicon wafer, plaster, plastic, and the like. In a case in which the damage indictor 10 is a glass plate (or a glass substrate), a length L of the glass plate 10 may range from 4 to 7 mm, a width W of the glass plate 10 may range from 1 to 3 mm, a thickness of the glass plate 10 may range from 80 to 150 µm, and a width of the crack guide through hole 10-1 may range from 0.7 to 2 mm$^2$.

The crack guide through hole 10-1 may be a diamond-shaped (for example, a lozenge-shaped or square-shaped) through hole, lengths of four sides of the diamond-shaped through hole may be equal, and lengths of two diagonal lines Dx and Dy of the diamond-shaped through hole 10-1 may range from 0.7 to 2 mm.

The corners of the crack guide through hole 10-1 are positioned to face the sides of the damage indictor (glass plate) 10. Also, an angle between a line linking the corners of the crack guide through hole 10-1 opposing each other and the sides of the damage indicator (glass plate) 10 may be a right angle. The crack guide through hole 10-1 may be formed at the center of the damage indicator (glass plate) 10.

A first pair of vertices (corners) of the crack guide through hole 10-1 facing (or opposing) each other are positioned in a length direction of the damage indicator 10, and a second pair of vertices (corners) of the crack guide through hole 10-1 facing each other are positioned in a width direction of the damage indicator 10.

An intended strain value may be implemented by fixing a length and a width of the damage indicator 10 and adjusting lengths of the two diagonal lines Dx and Dy of the crack guide through hole 10-1 and a thickness of the damage indicator 10.

A length, a width, and a thickness of the glass plate 10 and a width of the crack guide through hole 10-1 may be modified according to an intention of a designer. For example, when the length L of the damage indicator 10 is increased, stress of the damage indicator 10 is increased, and thus, stress applied to the damage indicator 10 is proportional to the length L. When the width W of the damage indicator 10 is increased, stress of the damage indicator 10 is reduced, and thus, stress applied to the damage indicator 10 is in inverse proportional to the width W. Thus, stress (stress due to strain) that may be measured may be adjusted by adjusting the length L and the width W of the damage indicator 10. A thin film may be formed on both surfaces or on one surface of the damage indicator 10.

The fixing member 20 may be an adhesive or a bonding agent fixedly attaching the damage indicator 10 to the PCB 200. The fixing member 20 may be gel type epoxy having high viscosity and fixedly attaching the damage indicator 10 to the PCB 200, and a gal type epoxy having high viscosity may be formed on the PCB 200 through a film mask such that an area and a height of the fixing member 20 may be uniformly maintained.

After the damage indicator 10 and the PCB 200 are attached (completely cured) by using the bonding agent, when the damage indicator 10 and the PCB 200 are separated, adhesion of the bonding agent disappears. The bonding agent may be a hot melt bonding agent or a liquid phase resin bonding agent which attaches the damage indicator 10 and the PCB 200. As the bonding agent, a hot melt bonding agent having a melting point having a predetermined temperature or higher may be used in order to enhance heat resistance. As the liquid phase resin bonding agent, a curable bonding agent such as a silicon resin, a fluorocarbon resin, and the like, may be used. As the bonding agent, a film type thermosetting bonding agent may also be used.

The hot melt bonding agent may be formed as any one of ethylenevinylacetate, polyisobutylene, polyimide, polyethyleneterephthalate, polypropylene, polyester, polyimide, and polyethylene.

After the damage indicator 10 and the PCB 200 are attached with the adhesive, when the damage indicator 10 and the PCB 200 are separated, the damage indicator 10 and the PCB 200 may be attached again. As a resin of the adhesive, acryl, silicon, PU, a fluoride resin, and the like, may be used. As the adhesive, an adhesive (double-sided adhesive tape) coated on both sides of a polyethylene terephthalate film, a polyimide film, aluminum foil, copper foil, paper, and the like, as a base may be used.

When a bonding agent is used as the fixing member 20, the damage indicator 10 may be attached to the PCB 200 by using the adhesive and subsequently heated at a temperature of 200° C. for 10 minutes to thermally cure the bonding agent.

Figure 2C:
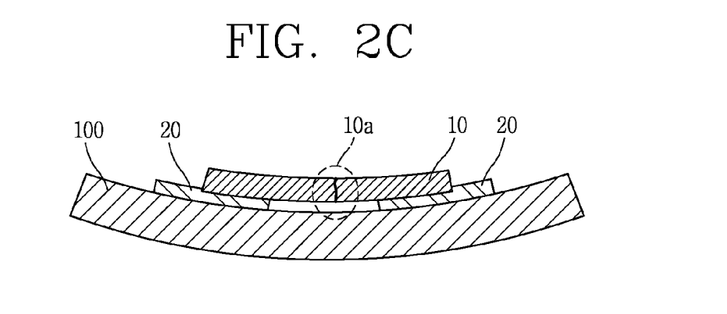
FIGS. 2C and 2D are views illustrating a state in which a strain inspection device of a PCB according to an embodiment of the present disclosure is cracked.
Figure 2D:
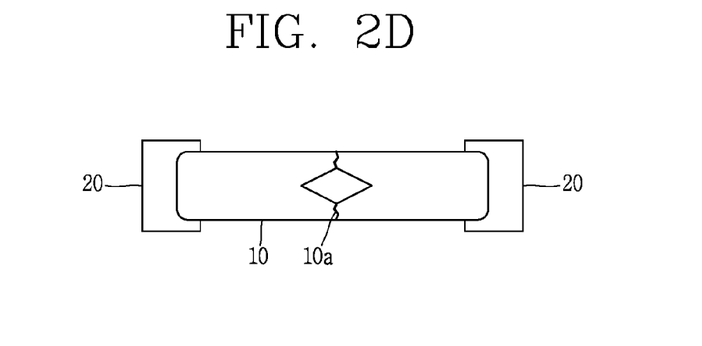

FIGS. 2C and 2D are views illustrating a state in which a strain inspection device of a PCB according to an embodiment of the present disclosure is cracked.

As illustrated in FIGS. 2C and 2D, the damage indicator 10 may be cracked (or damaged) due to bending (or deflection) of the PCB 200, and the PCB inspector may easily and quickly estimate a degree of damage of the PCB 200 by checking a degree 10a of crack or damage of the damage indicator 10.

Figure 3A:
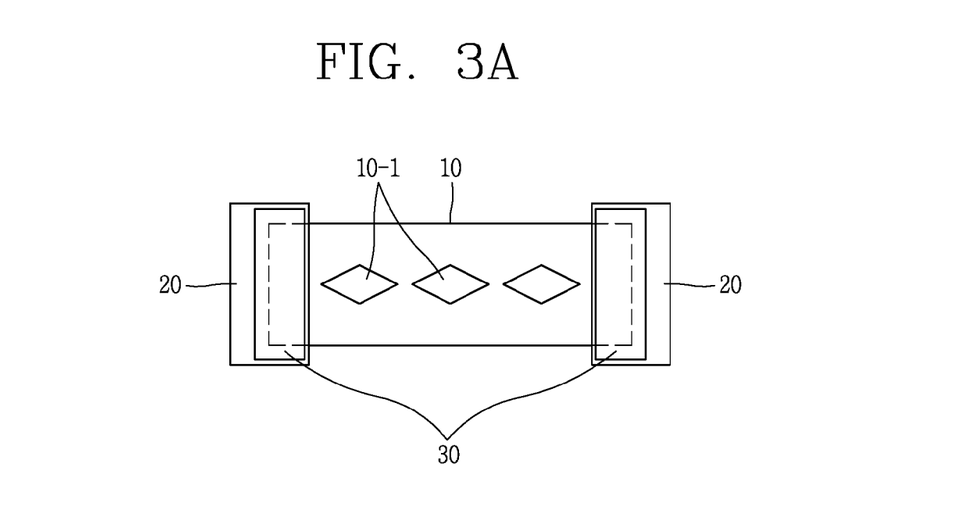
FIG. 3A is a side view illustrating a strain inspection device of a PCB according to another embodiment of the present disclosure is cracked.

FIG. 3A is a side view illustrating a strain inspection device of a PCB according to another embodiment of the present disclosure is cracked.

As illustrated in FIG. 3A, a PCB strain inspection device 100 according to another embodiment of the present disclosure includes a fixing member 20 and a damage indicator 10 fixed to the PCB 200 by the fixing member 20, having a plurality of crack guide through holes 10-1 disposed at a regular interval, and cracked (or damaged) along corners of any one of the plurality of crack guide through holes 10-1 due to bending (or deflection) of the PCB 200.

The PCB strain inspection device 100 according to another embodiment of the present disclosure may further include a second fixing member 30. The second fixing member 30 may be an adhesive or a bonding agent, and fixedly attaches edges of opposing sides of the damage indicator 10 in a length direction to the first fixing member 20. The second fixing member 30 is a film type thermosetting adhesive, and may be fixedly attached to the first fixing member 20 to cover the edges of opposing sides of the damage indicator 10 in the length direction.

When one or more crack guide through holes 10-1 are formed on the damage indicator 10, a small amount of stress than that of the damage indicator 10 in which the crack guide through hole 10-1 is not formed may be measured. For example, if 3000µε may be measured by the damage indicator 10 without the crack guide through hole 10-1, 300 to 2500µε or greater may be measured by the damage indicator 10 with the crack guide through hole 10-1.

One or a plurality of crack guide through holes 10-1 may be formed at uniform intervals in a length direction of the damage indicator 10.

One or a plurality of crack guide through holes 10-1 may be formed at different intervals in the length direction of the damage indicator 10.

The damage indicator 10 having the plurality of crack guide through holes 10-1 may be cracked along corners of one or a plurality of crack guide through holes 10-1 due to deformation of the PCB 200. For example, when a degree of deformation of the PCB 200 is small, the damage indicator 10 may be cracked along corners of one through hole, and when a degree of deformation of the PCB 200 is large, the damage indicator 10 may be cracked along corners of a plurality of through holes. Thus, when the damage indicator 10 is cracked or damaged along a plurality of through holes, rather than being cracked or damaged along one through hole, the PCB inspector may easily and quickly recognize that deformation of PCB 200 was severe. This will be described with reference to FIGS. 3B and 3C.

Figure 3B:
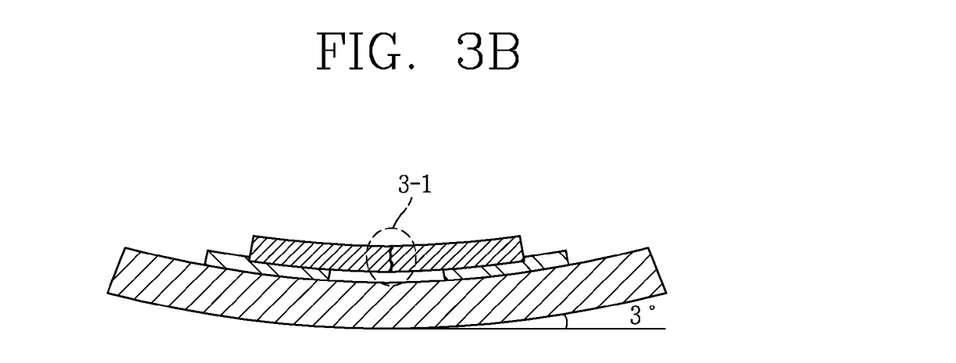
FIGS. 3B and 3C are views illustrating a state in which a strain inspection device of a PCB according to another embodiment of the present disclosure is cracked.
Figure 3C:
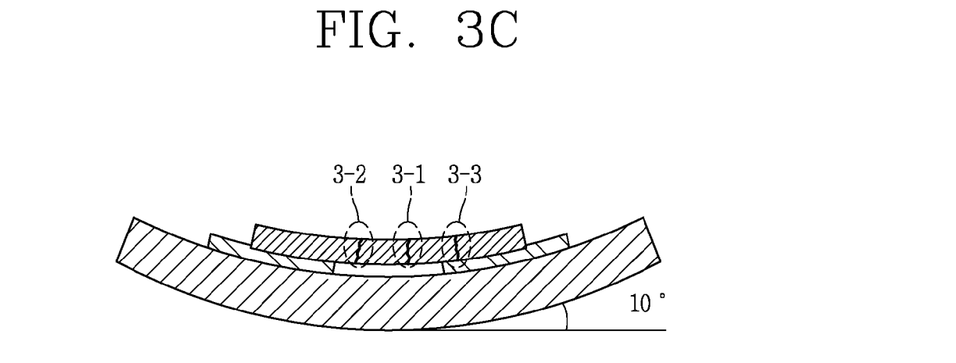

FIGS. 3B and 3C are views illustrating a state in which a strain inspection device of a PCB according to another embodiment of the present disclosure is cracked.

As illustrated in FIG. 3B, when it is assumed that the PCB 200 is instantly bent by 3 degrees by an external pressure (force), or the like, and restored, the damage indicator 10 may be cracked or damaged along corners of one through hole 3-1 among the plurality of through holes of the damage indicator 10.

As illustrated in FIG. 3C, when it is assumed that the PCB 200 is instantly bent by 20 degrees by an external pressure (force), or the like, and restored, the damage indicator 10 may be cracked or damaged along corners of all or some through holes 3-1, 3-2, and 3-3 among the plurality of through holes of the damage indicator 10.

Thus, the PCB inspector may easily and quickly recognize a degree of deformation of the PCB 200 by checking whether the damage indicator 10 has been cracked (or damage) along one through hole or along a plurality of through holes.

Figure 4:
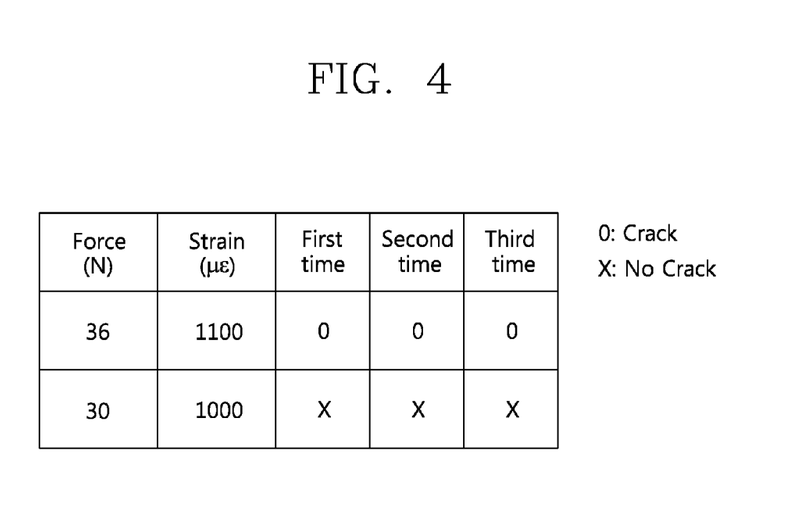
FIG. 4 is a view illustrating experiment results of a strain inspection device of a PCB according to embodiments of the present disclosure.

FIG. 4 is a view illustrating experiment results of a strain inspection device of a PCB according to embodiments of the present disclosure.

In FIG. 4, a crack state of the damage indicator 10 according to strain and force of the damage indicator 10 is illustrated. On the basis of the table illustrated in FIG. 4, a designer may manufacture a damage indicator of a desired standard. For example, when the damage indicator 10 used in the PCB strain inspection device 100 is glass plate, a length L of the glass plate 10 is 7 mm, a width W of the glass plate is 3 mm, and a thickness of the glass plate 10 is 0.08 mm. One crack guide through hole 10-1 is formed on the glass plate. The crack guide through hole 10-1 has a square shape as illustrated in FIG. 2B and is formed at the center of the glass plate such that virtual lines linking the corners diagonal to each other are perpendicular to each side of the glass plate. The diagonal lengths, that is, lengths of Dx and Dy, of the crack guide through hole 10-1, may be formed as 1.4 mm. The damage indicator 10 may be fixed to the PCB by using an epoxy resin. Thereafter, force of 36N and 30N may be applied to the PCB. The force of 36N applied to the PCB is measured as strain of about 1100με and the force of 30 N applied to the PCB is measured as strain of about 1000με. The damage indicator 10 fixed to the PCB was not damaged by the strain of about 1000με, but was damaged by the strain of about 1100με. Thus, the damage indicator 10 is a sensor damaged by stress exceeding the strain of 1000με when it is fixed to the PCB by using an epoxy resin.

Elements for determining a strain value of the damage indicator 10 may include a length, a width, a thickness, a surface treatment, and a material type of the damage indicator 10 and a shape of the crack guide through hole 10-1, and the like.

Also, a strain value of the damage indicator 10 may be determined according to a bonding technology (for example, thermal compression, natural drying, soldering, manual mounting, and the like) of bonding the damage indicator 10 to the PCB 200 by using the fixing members (for example, a bonding agent) 20 and 30. The strain value of the damage indicator 10 may be determined according to types (for example, a bonding film), a thickness, an area, bonding, and plating of the fixing members (for example, a bonding agent) 20 and 30.

Figure 5:
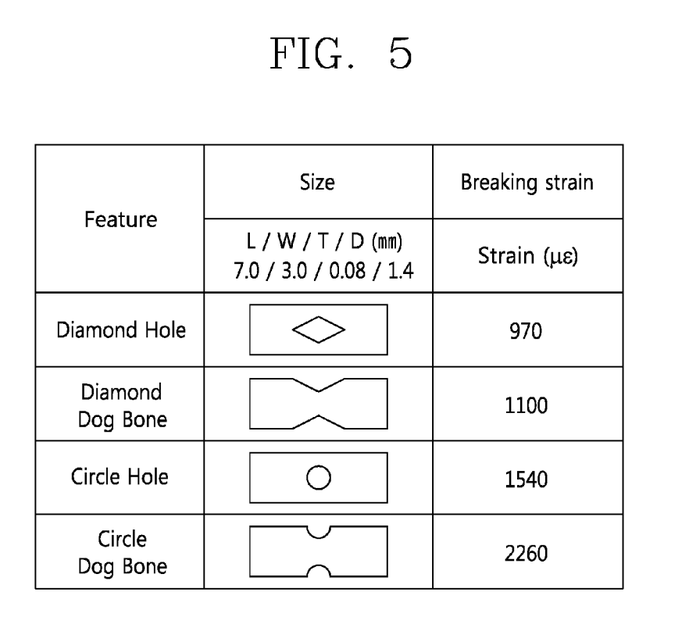
FIG. 5 is a view illustrating crack guide through holes having various shapes according to embodiments of the present disclosure.

FIG. 5 is a view illustrating crack guide through holes having various shapes according to embodiments of the present disclosure.

As illustrated in FIG. 5, the crack guide through hole according to embodiments of the present disclosure may be formed as triangular through holes (diamond dog bone) formed at a pair of sides of the damage indicator 10 in a length direction, a circular through hole (circle hole) formed at the center of the damage indicator 10, and semicircular through holes (circle dog bone) formed at a pair of sides of the damage indicator 10 in the length direction, as well as a diamond-shaped through hole. Strain values of the damage indicator 10 may be determined according to shapes of the crack guide through hole.

The diamond-shaped through hole has a small variation of stress values causing crack, compared with the triangular through hole (diamond dog bone), the circular through hole (circle hole), and the semicircular through hole (circle dog bone). That is, it can be seen that the diamond-shaped polygonal through hole is appropriate to be applied to the strain inspection device. For example, due to stress concentrating to sharp edge portions of the diamond-shaped through hole, the sharp edge portions of the diamond-shaped through hole may be a start point of cracking and cracking may be quickly in progress.

In case of the semicircular through hole and the circular through hole (circle hole), stress is distributed without a concentration point, and thus, the strain value is large and variations are severe. That is, the diamond-shaped through hole is easy to form cracking due to a distance from the corners of the through hole to the edges (sides) of the damage indicator 10, compared with the triangular through hole (diamond dog bone), the circular through hole (circle hole), and the semicircular through hole (circle dog bong).

Figure 6:
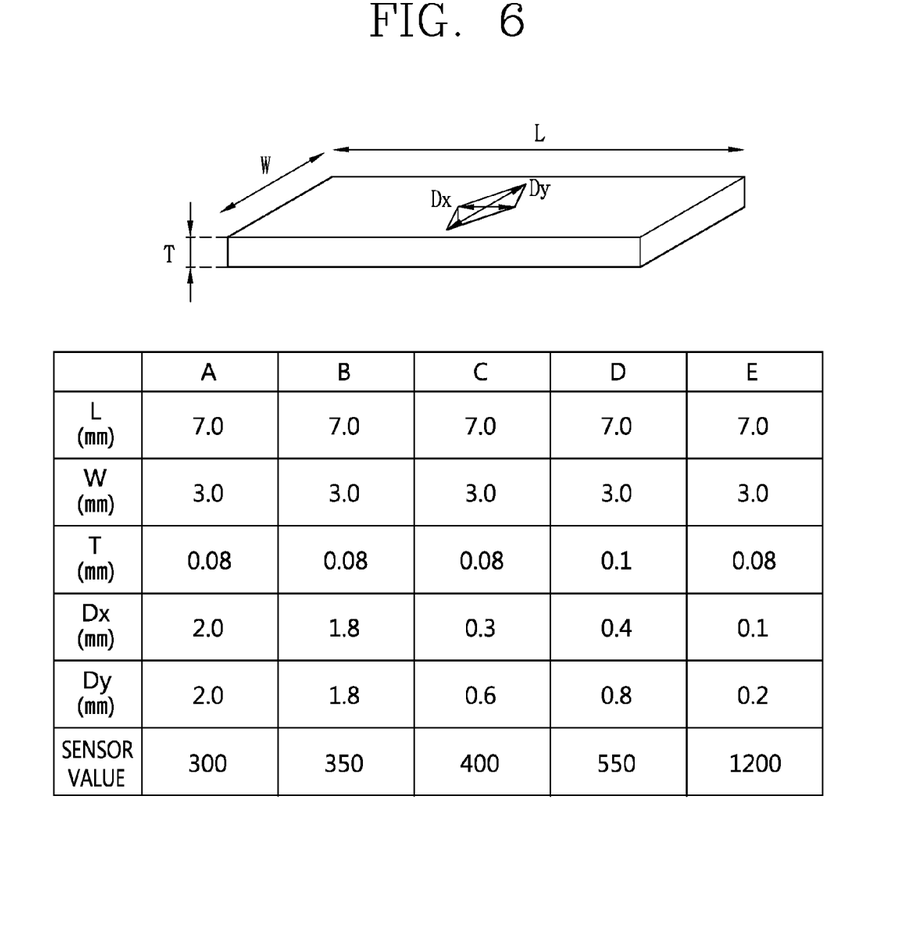
FIG. 6 is a view illustrating strain values (sensor values) according to sizes of diamond-shaped through holes according to embodiments of the present disclosure.

FIG. 6 is a view illustrating strain values (sensor values) according to sizes of diamond-shaped through holes according to embodiments of the present disclosure.

As illustrated in FIG. 6, according to results of experiment in which only the size of the diamond-shaped through hole was changed, while a length, a thickness, and a width of the damage indicator 10 were fixed, it can be seen that a sensor value of the damage indicator 10 can be increased by decreasing a size of the diamond-shaped through hole, and the sensor value of the damage indicator 10 can be decreased by increasing the size of the diamond-shaped through hole.

FIGS. 7A through 7E are views illustrating a sequential process of fixing a strain inspection device of a PCB to a PCB according to embodiments of the present disclosure.

Figure 7A:
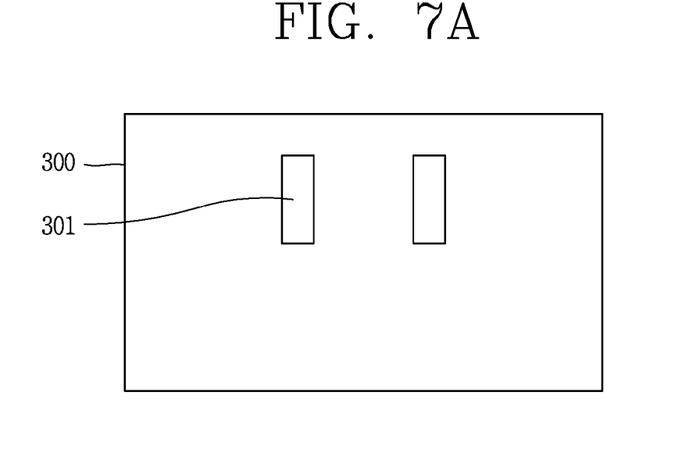
FIGS. 7A through 7E are views illustrating a sequential process of fixing a strain inspection device of a PCB to a PCB according to embodiments of the present disclosure.

As illustrated in FIG. 7A, a film mask 300 is manufactured in order to make an area and a height (thickness) of the fixing member (for example, a bonding agent) 20 uniform. The film mask 300 has a through hole 301 for applying the fixing member (for example, an epoxy bonding agent) 20 to the PCB 200, and a thickness of the film mask 300 and an area of the through hole of the film mask 300 are determined by the area and the height (thickness) of the fixing member (for example, an epoxy bonding agent) 20 desired by a designer. Since the fixing member 20 is applied through the through hole 301, the fixing member 20 is prevented from being excessively or insufficiently applied.

Figure 7B:
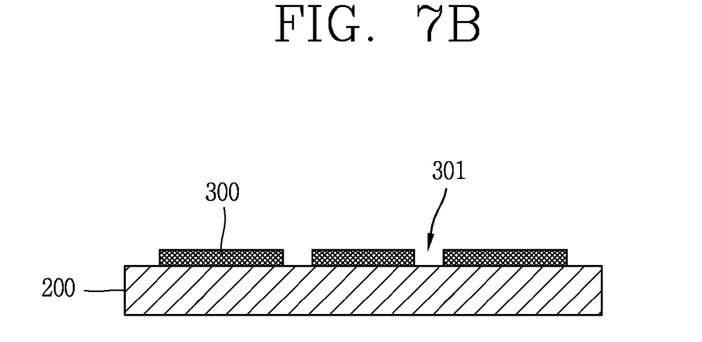

As illustrated in FIG. 7B, the through hole 301 of the film mask 300 is positioned on a preset position of the fixing member (for example, an epoxy bonding agent) 20 of the PCB 200.

Figure 7C:
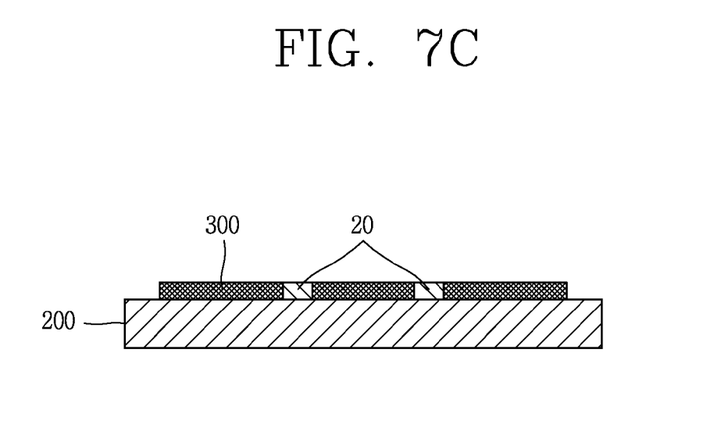

As illustrated in FIG. 7C, the fixing member (for example, a bonding agent) 20 is injected to the through hole 301 of the film mask 300. For example, by injecting an epoxy resin bonding agent 20 into the through hole 301 of the film mask 300, an amount of the epoxy resin bonding agent 20 may be adjusted. A double-sided tape may also be used as the fixing member 20.

Figure 7D:
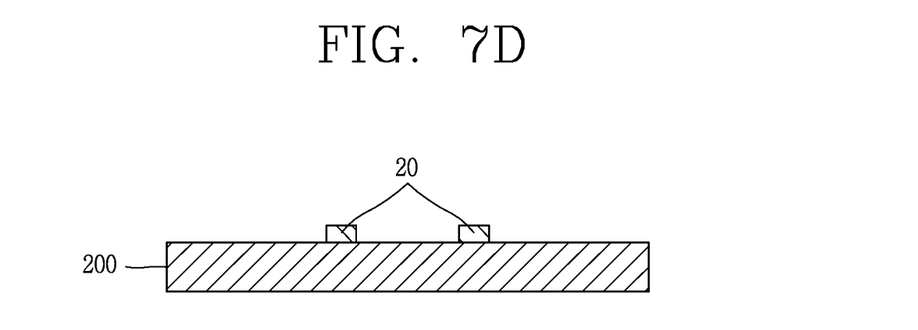
Figure 7E:
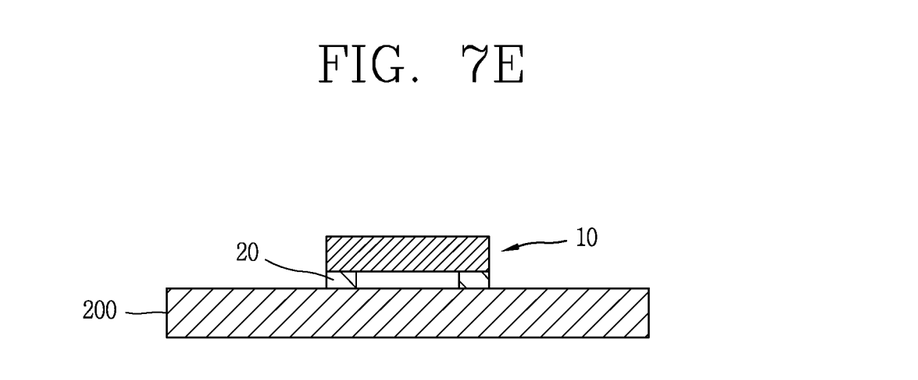

As illustrated in FIGS. 7D and 7E, after the film mask 300 positioned on the PCB 200 is removed, the damage indicator 10 is attached to the PCB 200 through the fixing member (for example, a bonding agent) 20.

As described above, the present disclosure may provide a PCB strain inspection device allowing a degree of strain (mechanical damage) that occurs due to pressure (force) applied to a PCB while the PCB is being assembled to be easily and quickly checked. For example, when the PCB strain inspection device fixedly attached to the PCB is damaged by a degree of bending of the PCB according to external pressure (force), a degree of damage to the PCB strain inspection device may be easily and quickly checked by an inspector, whereby a degree of damage to the PCB can be easily and quickly checked.

The present disclosure may provide a PCB strain inspection device in which a target strain reference value may be variously set by adjusting a size of a crack guide through hole and variations of strain values causing cracks are small by allowing the crack guide through hole to have a polygonal shape.

In the present disclosure, a degree of damage of the PCB can be accurately checked by using the PCB strain inspection device which is easily cracked or damaged by external pressure (force) applied to the PCB while the PCB is being assembled.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A strain inspection device of a printed circuit board (PCB), the device comprising:
    a first fixing member; and
    a damage indicator fixed to the PCB by the first fixing member, the damage indicator having a crack guide through hole, and the damage indicator being cracked or damaged along a corner of the crack guide through hole due to deformation of the PCB,
    wherein the crack guide through hole is provided at an inner center of the damage indicator, wherein the crack guide through hole includes at least a first corner and a second corner that opposes the first corner, wherein an angle between a first line linking the first and second corners of the crack guide through hole and a first side of the damage indicator is a right angle,
    wherein the damage indicator is a glass plate having the crack guide through hole, the glass plate is fixedly attached to the PCB by a bonding agent or an adhesive, the bonding agent or the adhesive is injected on the PCB through a through hole of a film mask, and wherein the first fixing member is the bonding agent or the adhesive fixedly attaching the damage indictor to the PCB.

2. The strain inspection device of claim 1, wherein at least a third corner of the crack guide through hole is positioned to face the first side of the damage indicator.

3. The strain inspection device of claim 1, wherein the crack guide through hole is a square through hole formed at the inner center of the damage indicator.

4. The strain inspection device of claim 1, wherein the crack guide through hole is a diamond-shaped through hole formed at the inner center of the damage indicator.

5. The strain inspection device of claim 1, wherein the crack guide through hole includes a third corner and a fourth corner that opposes the third corner,
    wherein a direction of the line linking the first and second corners of the crack guide through hole opposing each other is positioned as a length direction of the damage indicator, and a direction of a second line that links the third and fourth corners of the crack guide through hole is positioned as a width direction of the damage indicator.

6. The strain inspection device of claim 1, wherein the crack guide through hole is a through hole having a plurality of corners.

7. The strain inspection device of claim 1, wherein the crack guide through hole is formed in plurality at uniform intervals on the damage indicator.

8. The strain inspection device of claim 1, wherein one or a plurality of crack guide through holes are formed at uniform intervals on the damage indicator in a length direction of the damage indicator.

9. The strain inspection device of claim 1, wherein one or a plurality of crack guide through holes are formed at different intervals on the damage indicator in a length direction of the damage indicator.

10. The strain inspection device of claim 1, further comprising:
    a second fixing member attached to the first fixing member such that the second fixing member covers both edges of the damage indicator in a length direction.

11. The strain inspection device of claim 1, wherein the first fixing member is a film type thermosetting bonding agent or an epoxy resin bonding agent.

12. The strain inspection device of claim 1, wherein a material of the damage indicator is any one of glass, silicon wafer, plaster, and plastic.

13. The strain inspection device of claim 1,
    wherein a length of the damage indicator ranges from 4 to 7 mm, a width thereof ranges from 1 to 3 mm, and a thickness thereof ranges from 80 to 150 mm, and a width of the crack guide through hole ranges from 0.7 to 2 mm.

14. The strain inspection device of claim 1, wherein the crack guide through hole includes a third corner and a fourth corner that opposes the third corner.

15. The strain inspection device of claim 14, wherein an angle between a second line linking the third and fourth corners of the crack guide through hole and a second side of the damage indicator is a right angle.

16. A method for attaching a strain inspection device of a printed circuit board (PCB), the method comprising:
  forming a crack guide through hole having a corner on a glass plate; and
  fixedly attaching the glass plate with the crack guide through hole formed thereon to the PCB by using a bonding agent or an adhesive such that the glass plate is cracked along the corner of the crack guide through hole due to deformation of the PCB,
  wherein the attaching of the glass plate to the PCB comprises:
    positioning a film mask having a through hole on the PCB;
    injecting a bonding agent or an adhesive into the through hole of the film mask; and
    removing the film mask and subsequently fixedly attaching the glass plate to the PCB by using the bonding agent or the adhesive.

17. The method of claim 16, further comprising:
  applying heat to the bonding agent or the adhesive to thermally cure the bonding agent or the adhesive.

* * * * *